United States Patent
Singh et al.

(10) Patent No.: US 10,702,487 B2
(45) Date of Patent: Jul. 7, 2020

(54) PHARMACEUTICAL COMPOSITION FOR PREVENTION OF DIET INDUCED OBESITY

(71) Applicant: FRIMLINE PRIVATE LIMITED, Gujarat (IN)

(72) Inventors: Ankit Shyam Singh, Gujarat (IN); Vedprakash Mishra, Gujarat (IN); Neelima Tongra, Rajasthan (IN)

(73) Assignee: FRIMLINE PRIVATE LIMITED, Gujarat (IN)

(*) Notice: Subject to any disclaimer, the term of this patent is extended or adjusted under 35 U.S.C. 154(b) by 0 days.

(21) Appl. No.: 16/046,482

(22) Filed: Jul. 26, 2018

(65) Prior Publication Data

US 2019/0054046 A1    Feb. 21, 2019

(30) Foreign Application Priority Data

Aug. 19, 2017   (IN) .............................. 201721029447

(51) Int. Cl.
| | | |
|---|---|---|
| *A61K 31/16* | (2006.01) | |
| *A61K 31/195* | (2006.01) | |
| *A61K 31/198* | (2006.01) | |
| *A61K 31/197* | (2006.01) | |
| *A61P 3/04* | (2006.01) | |

(Continued)

(52) U.S. Cl.
CPC ............ *A61K 31/164* (2013.01); *A61K 9/485* (2013.01); *A61K 9/4858* (2013.01); *A61K 9/4866* (2013.01); *A61K 9/4875* (2013.01); *A61K 31/16* (2013.01); *A61K 31/195* (2013.01); *A61K 31/197* (2013.01); *A61K 31/198* (2013.01); *A61K 31/336* (2013.01); *A61K 31/353* (2013.01); *A61K 31/445* (2013.01);

(Continued)

(58) Field of Classification Search
None
See application file for complete search history.

(56) References Cited

U.S. PATENT DOCUMENTS 4,042,687 A * 8/1977 Gans ........................ A23J 3/342
                                                      514/4.8

FOREIGN PATENT DOCUMENTS

| CN | 102579414 A | 7/2012 |
|---|---|---|
| WO | 02/080860 A2 | 10/2002 |

(Continued)

OTHER PUBLICATIONS

Begriche et al., "beta-aminoisobutyric acid (BAIBA) prevents diet-induced obesity in mice with partial leptin deficiency", Obesity, vol. 16, #9, 2008 (Year: 2008).*

(Continued)

*Primary Examiner* — Kyung S Chang
(74) *Attorney, Agent, or Firm* — Baker & Hostetler LLP

(57) ABSTRACT

The present invention relates to a pharmaceutical composition/formulation for the prevention of diet induced obesity. More particularly, the invention relates to a composition/formulation comprising a synergistic combination of Oleoylethanolamide (OEA) and other natural ingredients can be used for treatment of obesity and its related disorders associated with fat metabolism like non-alcoholic steatohepatitis (NASH), non-alcoholic fatty liver disease (NAFLD). This can also be helpful in controlling obesity by way of maintaining body weight. The invention also provides various formulations and methods of preparing the same.

12 Claims, 3 Drawing Sheets

(51) Int. Cl.
| | |
|---|---|
| A61K 31/164 | (2006.01) |
| A61K 31/445 | (2006.01) |
| A61K 9/48 | (2006.01) |
| A61K 31/336 | (2006.01) |
| A61K 31/353 | (2006.01) |
| A61K 31/45 | (2006.01) |
| A61K 45/06 | (2006.01) |

(52) U.S. Cl.
CPC .............. *A61K 31/45* (2013.01); *A61K 45/06* (2013.01); *A61P 3/04* (2018.01)

(56) References Cited

FOREIGN PATENT DOCUMENTS

| | | |
|---|---|---|
| WO | 2004/034968 A2 | 4/2004 |
| WO | 2004/045307 A2 | 6/2004 |
| WO | 2004/078113 A2 | 9/2004 |
| WO | 2005/046580 A2 | 5/2005 |
| WO | 2007/006319 A2 | 1/2007 |
| WO | WO-2009093737 A1 * | 7/2009 ........... A61K 31/197 |
| WO | 2009/142713 A1 | 11/2009 |
| WO | 2012/015704 A2 | 2/2012 |
| WO | 2012/090225 A2 | 7/2012 |
| WO | 2012/154711 A1 | 11/2012 |
| WO | 2013/028570 A2 | 2/2013 |
| WO | 2014/017936 A2 | 1/2014 |
| WO | 2014/037546 A1 | 3/2014 |
| WO | 2015/007613 A1 | 1/2015 |
| WO | 2015/007615 A1 | 1/2015 |
| WO | 2015/012708 A1 | 1/2015 |
| WO | 2015/016728 A1 | 2/2015 |
| WO | 2015/157313 A1 | 10/2015 |
| WO | 2016/185468 A1 | 11/2016 |
| WO | 2017/025588 A1 | 2/2017 |

OTHER PUBLICATIONS

WO2009/093737A1—Google English translation. (Year: 2009).*
Tsuduki et al., "Intake of mulberry 1-deoxynojirimycin (DNJ) prevents diet-induced obesity through increase in adiponectin in mice", Food Chemistry, vol. 139. No. 1-4, 2013, pp. 16-23. (Year: 2013).*
Yun et al., "Possible anti-obesity therapeutics from nature—A review" Phytochemistry, vol. 71, No. 14-15, 2010, pp. 1625-1641. (Year: 2010).*
Brunt et al.; "Nonalcoholic Steatohepatitis: A Proposal for Grading and Staging the Histological Lesions"; The American Journal of Gastroenterlogy; vol. 94; No. 9; 1999; pp. 2467-2474.
Elizabeth Brunt; "Nonalcoholic Steatohepatitis: Definition and Pathology"; Seminars in Liver Disease; vol. 2; No. 1; 2001; pp. 3-16.
Takahashi et al.; "Animal Models of Nonalcoholic Fatty Liver Disease/Nonalcoholic Steatohepatitis"; World Journal of Gastroenterlogy; Issue 19; vol. 18; May 21, 2012; pp. 2300-2308.
National Heart, Lung and Blood Institute, Clinical Guidelines on the Identification, Evaluation, and Treatment of Overweight and Obesity in Adults: The Evidence Report; NIH Publication No. 98/4083; Sep. 1998.
Cooke et al.; "The Obesity Pipeline: Current Strategies in the Development of Anti-Obesity Drugs"; Nature Reviews; Drug Discovery; vol. 5; Nov. 2006; pp. 919-931.
Questions and Answers on the Suspension of Medicines Containing Sibutramine—Outcome of a Procedure Under Article 107 of Directive 2001/83/EC; European Medicines Agency; Science Medicines Health; Jan. 21, 2009; pp. 1-3.
Colombano et al.; "O-(Triazoly)methyl Carbamates as a Novel and Potent Class of FAAH Inhibitors"; ChemMedChem Author Manuscript available in PMC Feb. 1, 2016; pp. 1-36.
Otrubova et al.; "The Discovery and Development of Inhibitors of Fatty Acid Amide Hydrolase (FAAH)"; Bioorg Med Chem Lett. Author Manuscript available in PMC Aug. 15, 2012; pp. 1-47.
Eddleston et al.; "Implications of the BIA-102474-101 Study for Review of First-Intro-Human Clinical Trails"; British Journal of Clinical Pharmacology; No. 81; 2016; pp. 582-586.
Kaur et al.; "What Failed BIA 10-2474 Phase I Clinical Trial? Global Speculations and Recommendations for Future Phase I Trials"; J. Pharmacol Pharmacother; vol. 7; No. 3; Jul.-Sep. 2016; pp. 120-126.
Mallet et al.; "FAAH Inhibitors in the Limelight, But Regrettably"; International Journal of Clinical Pharmacology and Therapeutics, vol. 54; No. 7; 2016; pp. 498-501.

* cited by examiner

PHARMACEUTICAL COMPOSITION FOR PREVENTION OF DIET INDUCED OBESITY

FIELD OF THE INVENTION

The present invention relates to a pharmaceutical composition/formulation for use in the prevention of diet induced obesity. More particularly, the invention relates to a composition/formulation comprising a synergistic combination of Oleoylethanolamide (OEA) and other natural ingredients for the treatment of obesity and its related disorders associated with fat metabolism like non-alcoholic steatohepatitis (NASH) and non-alcoholic fatty liver disease (NAFLD). This can also be helpful in controlling obesity by way of maintaining body weight. The invention also provides various formulations and methods of preparing the same.

BACKGROUND OF THE INVENTION

Obesity has become one of the most significant public health problems faced by the world today. Obesity is a serious health problem involving multiple factors. Evidence suggests obesity also involves appetite regulation and energy metabolism for control. In the United States, the prevalence of obesity has risen by 32% in adults and 40% in children over last two decades. Obesity is not just being overweight. It is a metabolic disorder due to the accumulation of excess dietary calories into visceral fat and the release of high concentrations of free fatty acids into various organs. As defined by the World Health Organization (WHO), a body mass index (BMI) greater than 25 is classified as overweight and a BMI greater than 30 as obesity. According to the global statistics, the population of overweight and obese individuals is approximately over 4.5 billion, of which approximately 27% is obese.

The increasing prevalence of obesity is a worldwide threat because it enhances the risk of various metabolic disorders and diseases such as insulin resistance, type 2 diabetes, hyperlipaemia, coronary heart disease, steatosis cardiovascular diseases, diabetes, chronic lower respiratory diseases, chronic hepatic disease and liver cirrhosis, hypertensive diseases, renal disease and NASH, NAFLD, and some type of cancers. Obesity not only increases mortality and causes huge medical complications, but also affects the life style.

The prevalence of NAFLD has increased in parallel with incidence of central obesity and is now the most common fatty liver disease in developed countries. NAFLD is defined as the presence of hepatic steatosis, with or without inflammation and fibrosis, in the absence of alcohol history. NAFLD is subdivided into NAFL and NASH. In NAFL, hepatic steatosis is present without evidence of significant inflammation, whereas in NASH, hepatic steatosis is associated with hepatic inflammation that may be histologically indistinguishable from alcoholic steatohepatitis.

The histological spectrum of NAFLD includes the presence of steatosis alone, fatty liver and inflammation. NASH is a more serious chronic liver disease characterized by excessive fat accumulation in the liver that induces chronic inflammation which leads to progressive fibrosis (scarring) that can lead to cirrhosis, hepatocellular carcinoma (HCC), eventual liver failure and death (Brunt et al., Am. J. Gastroenterol. 94:2467-2474, 1999; Brunt, Semin. Liver Dis. 21:3-16, 2001; Takahashi Y et al., World J Gastroenterol, 18:2300-2308, 2012).

NAFLD is generally recognized to be associated with metabolic syndrome such as insulin resistance, diabetes mellitus type 2, hyperlipidemia, hypertension and obesity. It is usually seen in people who are overweight or obese. NAFLD affects 30% of the world population and about 80% of obese people. NASH is more common in women and the most common cause is obesity. Recent studies also indicate that Overweight and obesity were strongly and progressively associated with an increased incidence of NAFLD.

NASH is a progressive, severe form of NAFLD. Over last 10-year period, up to 20% of patients with NASH will develop cirrhosis of the liver, and around 10% will suffer death related to liver disease. NASH progresses to cirrhosis in around 15-20% of affected individuals and is now one of the leading indications for liver transplantation in the United States. At present there are no approved therapies for NASH.

Despite the continuous increase in obesity incidences attributed to chronic liver diseases like NAFLD and NASH in all developed countries, limited pharmacological therapies are currently available to treat obesity or its related disorders in an efficacious and safe manner for the public.

Decreasing nutrient absorption, inhibition of appetite, and increasing thermogenesis are considered possible pharmacological methods for treating obesity. All of them have their substantial drawbacks. Decreasing nutrient absorption (e.g., inducing fat malabsorption) may cause gastrointestinal discomfort. Inhibition of appetite is usually expected to involve actions on brain structures, thus leading to problems of brain targeting and contamination of other tissues. Increasing thermogenesis may also have serious side effects.

Obesity Treatment

For effective treatment of obesity, current treatment modalities typically include diet and exercise programs, lifestyle management, pharmacotherapy and surgery. Treatment decisions are usually made based on severity of obesity, seriousness of associated medical conditions, subject risk status and subject expectations. Notable improvements in cardiovascular risk and the incidence of diabetes have been observed with weight loss of 5-10% of body weight, supporting clinical guidelines for the treatment of obesity that recommend a target threshold of 10% reduction in body weight from baseline values. Unfortunately, the available pharmacological therapies to facilitate weight loss fail to provide adequate benefit to many obese subjects because of side effects, contraindications or lack of positive response (National Heart, Lung and Blood Institute, Clinical guidelines on the identification, evaluation, and treatment of overweight and obesity in adults: the evidence report, NIH Publication No. 98-4083, September 1998).

Obesity Treatment by Medicines (Drugs)

Current treatment options for type IIb hyperlipidemia mostly seen in obese persons are limited. While statins are very effective at lowering LDL-C, they are generally not very effective at lowering triglyceride levels. Some statins at high dose levels, for example atorvastatin at 80 mg, significantly lower triglyceride levels. However, high dose statin therapy can cause muscle pain (myalgia) and is often not well tolerated by patients. In addition, high dose statin therapy carries with it an increased risk for serious muscle toxicity such as rhabdomyolysis. Another treatment which typically includes administering a combination of a cholesterol lowering agent, such as a statin, and a triglyceride lowering agent, such as a fibrate, niacin or fish oil. However, the commonly used triglyceride lowering agents may not be convenient or may not be well tolerated, for example, fibrates are associated with myalgia and an increased risk of muscle toxicity, fish oil needs to be taken multiple times daily, and niacin causes flushing particularly when administered in combination with statins.

The most popular over-the counter drugs for the treatment of obesity are phenylpropanolamine and ephedrine, and the most popular prescription drug, is fenfluramine. These drugs were withdrawn from the marketplace as a result of safety concerns. Drugs currently approved for the long-term treatment of obesity fall into two categories:

1. Amphetamines and sibutramine that act on the hypothalamus to control appetite stimulation in the CNS. (CNS appetite suppressants).
2. Orlistat that is a lipase inhibitor that blocks gastrointestinal absorption of fat and decreases energy uptake (Gut Lipase Inhibitors [Cooke et al 2006 Nat Rev Drug Discov 5:919-31].).

Common side effects associated with these drugs include tachycardia, hypertension, fecal incontinence and/or cardiac valvopathy, making anti-obesity drug development of paramount importance.

Although appetite suppressants and gut lipase inhibitors work through very different mechanisms, they share the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

For example, orlistat, sibutramine, and liraglutide, i.e., compounds used so far for treating metabolic syndrome or obesity, cause a series of severe side effects. In particular, the European Medicines Agency (EMA) has reviewed the safety and effectiveness of sibutramine and came to the conclusion that the benefits of sibutramine do not outweigh its risks, and that all marketing authorizations for medicines containing sibutramine should be suspended throughout Europe (cf. "Questions and answers on the suspension of medicines containing sibutramine—Outcome of a procedure under Article 107 of Directive 2001/83/EC", EMA/808179/2009). Furthermore, the primary side effects of orlistat comprise steatorrhea, fecal incontinence and the inhibition of absorption of fat-soluble vitamins thereby forcing the patient who takes orlistat to:
(i) avoid foods with high fat content and
(ii) separately take dietary supplements containing fat-soluble vitamins and other fat-soluble nutrients.

Obesity Treatment by Surgery

Bariatric surgery may be considered as a weight loss intervention for subjects at or exceeding a BMI of 40 kg/m$^2$. Subjects with a BMI of 35 kg/m$^2$ and with an associated serious medical condition are also candidates for this treatment option. Unfortunately, postoperative complications commonly result from bariatric surgical procedures, including bleeding, embolism or thrombosis, wound complications, deep infections, pulmonary complications, and gastrointestinal obstruction; reoperation during the postoperative period is sometimes necessary to address these complications. Major and serious adverse outcomes associated with bariatric surgery are common, observed in approximately 4 percent of procedures performed (including death in 0.3 to 2 percent of all subjects receiving laparoscopic banding or bypass surgeries, respectively).

Lifestyle

The most important recommendations given to persons with this disease are aerobic exercise, manipulations of diet and eating behavior, and reducing their weight (if obese or overweight). Since lifestyle modification has not been proven effective, therapeutic strategies are required. However, potent and safe therapeutic strategies to combat these diseases are inadequate. Currently there are no effective pharmaceutical treatments for this pandemic problem. Although surgical procedures can reduce weight by 50-90%, it is restricted due to the risk of surgery and associated side effects. Therefore, there is still a need for the development of alternative and/or improved therapeutic strategies for the treatment obesity and its related disorders.

NAFLD Treatment by Medicines

Treatment of the symptoms of NAFLD/NASH include lipid lowering medications, insulin sensitizing (medications), and the reduction of inflammation via anti-oxidant medications (such as vitamin E, selenium, and betaine), anti-apoptotic medications, and anti-cytokine medications, it may also include reduction of total cholesterol level, weight loss, control of any underlying diabetes, reduction or elimination of alcohol consumption, treatment of high blood pressure, and regular exercise. (American College of Gastroenterology; WebMD).

The most important recommendations given to persons with this disease are to reduce their weight (if obese or overweight), follow a balanced and healthy diet, increase physical activity, avoid alcohol, and avoid unnecessary medications. Another experimental approach to treat NAFLD/NASH is the use of newer antidiabetic medications—even in persons without diabetes. The primary goal for the clinical management of NAFLD/NASH is to reduce the risk of cardiovascular disease and type II diabetes. The risks of these diseases are highly diminished by reducing triglyceride levels in the blood including LDL cholesterol, reducing blood pressure, and reducing blood glucose levels.

Current treatments target either insulin resistance (e.g., metformin, thiazolidinediones) or insulin release from the beta cell (e.g., sulfonylureas, exenatide). However, these treatments suffer from various deficiencies, including side effects, limited efficacy, and undesirable long-term effects. However, there are currently no approved treatments for NASH/NAFLD itself.

NAFLD may go on to cause cirrhosis or liver cancer and as such early and effective treatment is essential. Otherwise, Liver transplantation is the only curative option for patients with advanced liver cirrhosis. However, this procedure can only be applied to a minority of patients due to the presence of surgical contraindications and organ scarcity.

While there are been continued advancements, there remains a pressing need for more safe, effective and improved therapies for treatment of obesity and its related diseases like NASH/NAFLD. Thus, a naturally occurring, orally active compound(s) that will reduce obesity and its related disorders is desired.

Requirement of Natural Active Ingredients

OEA is an endogenous peroxisome proliferator-activated receptor alpha (PPAR-α) agonist, and is the result of a combination of oleic acid and ethanolamine. OEA is a naturally occurring lipid mediator that inhibits food intake and body weight gain and therefore has been a molecule of recent intense scientific interest in the search for therapeutic strategies for the treatment of human obesity. OEA is a fatty acid metabolite that is produced by the gut to signal to the brain the sensation of being full, thus to regulate appetite and healthy body fat. OEA helps regulate lipid metabolism, helps control hunger by sending appetite suppressant messages to the brain and has been shown to help lower both triglyceride and blood cholesterol levels.

β-aminoisobutyric acid (BAIBA) is a non-protein β-amino acid, a catabolite of thymine, which is further degraded into propionyl-CoA, methylmalonyl-CoA and succinyl-CoA within mitochondria, especially in liver. BAIBA can also be generated by catabolism of the branched-chain amino acid valine. BAIBA reduces body fat percentage through increased fatty acid oxidation (FAO) and decreased de novo lipogenesis in liver in mice. BAIBA enhances the browning of white adipose tissue and FAO in the liver via peroxisome proliferator-activated receptor α (PPARα), and may contribute to exercise-induced protection from metabolic diseases. In humans, plasma BAIBA concentrations are increased with exercise and inversely associated with metabolic risk factors. BAIBA may thus contribute to exercise-induced protection from metabolic diseases.

Anti-oxidants also play an important role in the treatment of obesity. An increase in leptin leads to an increase in adhesion molecules; adipocytes recruit monocytes which are then transformed into macrophages. Macrophages are capable of producing large amounts of oxidants such as peroxynitrite. An obesity-associated increase in oxidative stress has been examined by different methods-measurements of thiobarbituric reactive acid substances (TBARS), malondialdehyde formation (MDA), oxidized LDL, oxidized urinary albumin, peroxide estimated from reactive oxygen assays, and the formation of carbonyl proteins in erythrocytes. A review of the literature shows that in most studies, obesity and type 2 diabetes are associated with an increase in oxidative stress. Thus, the oxidative stress is also associated with weight loss rather than diet alone. Given that obesity and type 2 diabetes are associated with increased oxidative stress, there is a need of an anti-oxidant to manage the excessive generated free radicals or toxins.

α-Glucosidase inhibitors can be used as a new class of antidiabetic drug. By competitively inhibiting glycosidase activity, these inhibitors help to prevent the fast breakdown of sugars and thereby control the blood sugar level. In the 1980s, α-glucosidase inhibitors became a new class of antidiabetic drug. α-Glucosidase inhibitors slow down the process of digestion and absorption of carbohydrates by competitively blocking the activity of glucosidase. All of them contain sugar moieties and their synthesis involves tedious multistep procedures. Moreover, clinically chemically synthesized α-glucosidase inhibitors have been associated with serious gastrointestinal side effects. Therefore, it is necessary to search for alternatives that can display α-glucosidase inhibitory activity but without side reactions.

I-deoxynojirimycin (DNJ) is a glucose analogue with a secondary amine group instead of an oxygen atom in the pyranose ring of glucose. DNJ potently inhibits α-glucosidase in the small intestine by binding to the active center of α-glucosidase. DNJ has also been found in the leaves and fruits of M. alba, suggesting that the legendary antidiabetic effect of mulberry leaves may be attributed to DNJ, which inhibits postprandial hyperglycemia by inhibiting α-glucosidase in the small intestine. Use of DNJ-rich mulberry leaf extract modestly decreased Triglyceride level after intake of long duration (12 weeks), although the decrease was not statistically significant. Several studies have demonstrated that phytochemicals from natural resources provide new opportunities for treating diabetes. Mulberry leaf extracts have been used in China and other Asian countries to treat diabetes on the basis of reports of antidiabetic effects in experimental animals.

Cannabinoid-based medicines have therapeutic potential for the treatment of pain. Augmentation of levels of endocannabinoids with inhibitors of fatty acid amide hydrolase (FAAH) is analgesic. Fatty acid amide hydrolase (FAAH) is a membrane-bound serine hydrolase that belongs to the amidase signature family of hydrolases. FAAH enzyme breaks down fatty acid amides such as anandamide (N-arachidonoylethanolamine), N-oleoylethanolamide (N-OEA), N-palmitoylethanolamide (N-PEA) and oleamide. FAAH belongs to a large and diverse class of enzymes referred to as the amidase signature (AS) family. FAAH Inhibitors are a class of molecules that inactivate the Fatty Acid Amine Hydrolase Enzymes by preventing the hydrolysis of anandamide, oleoylethanolamide and palmitoylethanolamide and thereby increasing their endogenous levels. Known chemically synthesized FAAH inhibitors are BIA 10-2474, URB524, URB-597, URB694, URB937, etc. These inhibitors are disclosed in Colombano et al. in the published article titled "O-(Triazolyl) methyl carbamates as a novel and potent class of fatty acid amide hydrolase (FAAH) inhibitors" and in the published article by Otrubova et al. titled "The discovery and development of inhibitors of fatty acid amide hydrolase (FAAH).

RELATED PRIOR ARTS

WO02080860 refers to a method of reducing food intake in a mammal by using OEA.

WO200434968 refers to a method of reducing food consumption in a mammal by administering PPARα agonist and chemically synthesized CB 1 receptor Antagonist.

WO2004045307 describes food products and supplements comprising OEA for inducing satiety and decreasing weight.

WO2004078113 refers to a method of preventing or treating obesity and obesity-related complications by administering a Cox-2 inhibitor in combination with one or more weight-loss agents selected from the group consisting of OEA.

WO200546580 describes the use of OEA for reducing body weight, modulating body lipid metabolism and reducing food intake.

WO2007006319 discloses the use of an appetite suppressing or satiety inducing agent such as OEA for the manufacture of a pharmaceutical composition for the prophylaxis or therapeutic treatment of diseases or disorders associated with impaired appetite regulation in a mammal.

WO2009142713 refers to a method for reducing lipid absorption by an animal comprising administering one or more fatty acid alkanolamides such as OEA to the animal in an amount effective for reducing lipid absorption by the animal.

WO201290225 discloses a fixed dose pharmaceutical composition comprising co-crystals of Metformin or its pharmaceutically acceptable salts and OEA with other antidiabetic agents.

WO2012154711 discloses a composition comprising OEA in a therapeutically effective amount for promoting lean body mass growth.

CN102579414 refers to the use of OEA as an appetite suppressant

WO201437546 discloses a flowable emulsion comprising Oleoylethanolamide, oil, water and an emulsifier as well as free-flowing powder comprising Oleoylethanolamide.

WO2016185468 discloses a pharmaceutical composition comprising a therapeutically-effective amount of a mixture of at least one opioid or a salt thereof and at least one N-acylethanolamine or a salt thereof, wherein the molar ratio between the opioid or the salt thereof and the N-acylethanolamine or the salt thereof is between about 1:1 to about 1:100.

WO201725588 discloses a nanoparticle comprising at least one of a biocompatible lipid and a lipophilic therapeutic such as Oleoylethanolamide, lubricating and/or diagnostic agent, wherein the nanoparticle has a surface comprising a water soluble polymer.

There are several patent applications (WO 2012/015704, WO 2013/028570, WO 2014/017936, WO 2015/07613, WO 2015/07615, WO 2015/012708, WO 2015/016728, WO 2015/157313), which disclose chemically synthesized different types of FAAH inhibitors which elevate OEA level. However, these chemically synthesized FAAH inhibitors may have side effects upon administration in human or animals. Several studies reveal the serious side-effects (including death) of chemically synthesized FAAH inhibitors. Some of them include Eddleston Michael et al; "Implications of the BIA-102474-101 study for review of first-into-human clinical trials", Br J Clin Pharmacol (2016) 81 582-586; Mallet et. al.; "FAAH inhibitors in the limelight, but regrettably", International Journal of Clinical Pharmacology and Therapeutics, Vol. 54—No. 7/2016 (498-501); and Kaur et al." "What failed BIA 10-2474 Phase I clinical trial? Global speculations and recommendations for future Phase I trials", J Pharmacol Pharmacotherapy. 2016 July-September; 7(3): 120-126.

In particular, there are numerous challenges for the treatment of obesity and its related disorder associated with fat metabolism like NAFLD, NASH, such as in the prior arts disclosed above. Further, as discussed above, currently available treatments for obesity and its related disorders lack efficacy and are complicated due to relapse rates and a wide range of side effects such as endothelial dysfunction and cardiovascular risk. The inventors of the subject application revealed an utmost need to provide treatment for obese patients in an efficacious and safe manner. Therefore, the inventors have developed a pharmaceutical composition/formulation comprising a synergistic combination of OEA with other active ingredients which control diet induced obesity and also treat other metabolic disorders associated with fat metabolism like NASH, NAFLD with acceptable safety profile.

There is also a need for effective composition/formulation to treat overweight as well as to maintain weight loss.

Consequently, there is also an urgent need to develop therapies to delay development, prevent formation or reverse the condition of a fatty liver. The currently available treatments for NAFLD and NASH are quite limited and there arise a need for safe and effective treatment for patients suffering from NAFLD and NASH.

Despite the efforts in the prior arts, treatment for obesity and related disorders remains a challenge. It would therefore be useful to provide an effective and safe treatment to avoid the obesity related complications.

SUMMARY OF THE INVENTION

The present invention provides a pharmaceutical composition/formulation comprising a synergistic combination of oleoylethanolamide (OEA) and other natural active ingredients selected from natural β-aminoisobutyric acid (BAIBA), natural antioxidant, natural alpha-glucosidase inhibitor, natural Fatty Acid Amine Hydrolase Inhibitor (FAAH)) or combination thereof.

In a preferred aspect, the present invention provides a pharmaceutical composition/formulation comprising a synergistic combination of OEA and other natural active ingredients selected from natural BAIBA and/or natural antioxidant.

In a further preferred aspect, the pharmaceutical composition/formulation of the present invention additionally comprises natural FAAH inhibitor or natural alpha-glucosidase inhibitor or a combination thereof.

In a preferred aspect, the present invention provides a pharmaceutical composition/formulation comprising a synergistic combination for the treatment of diet induced obesity and its related disorder associated with fat metabolism such as NAFLD, hepatic steatosis. NASH, fibrosis, cirrhosis, and hepatocellular carcinoma (HCC). The said composition/formulation comprises a synergistic combination of OEA with other natural active ingredients selected from natural BAIBA, natural antioxidant, natural alpha-glucosidase inhibitor, natural FAAH Inhibitor or combination thereof and pharmaceutically acceptable excipients.

In another aspect of the present invention, a process for the preparation of a composition/formulation is described. The process comprises (a) individually weighing OEA, natural BAIBA, natural anti-oxidant, diluent and glidant in separate containers, sieving the ingredients separately through a suitable sieve, (b) mixing the previously weighed ingredients, (c) preparing a dough by adding a binder solution to the mixed ingredients and sieving to obtain granules, (d) drying the granules till the level of dryness (LOD) is reduced to less than 1.5% w/w to obtain semi dried granules, and (e) sieving the semi dried granules through a suitable sieve to obtain the composition/formulation. The process further comprises adding lubricants or glidants to the semi dried granules and filling the granules in Hydroxypropylmethyl cellulose (HPMC) capsule shells and sealing.

In a preferred aspect, the application provides a process for preparing the composition/formulation of the present invention. The process comprises sifting previously weighed OEA, natural BAIBA(s), diluent(s), and glidant(s) separately through a sieve, mixing the contents to obtain a mixture, preparing a binder solution, adding the binder solution to the mixture obtained above and obtaining granules, drying the obtained granules to obtain semi dried granules and sifting the semi dried granules through a sieve, sifting previously weighed lubricant(s) or glidant(s) separately through a sieve and mixing with the sifted semi dried granules to obtain a blend of the composition/formulation. The blend is further filled and sealed with HPMC capsule shells.

DETAILED DESCRIPTION OF THE INVENTION

Figure 1:
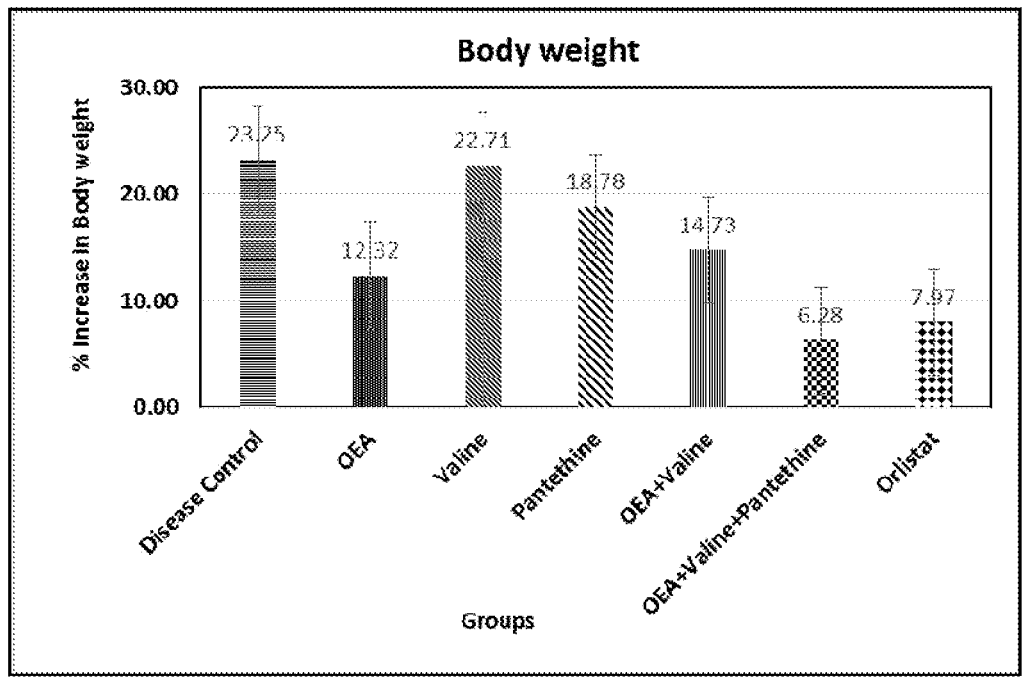
FIG. 1: A comparative study of the percentage increase in body weight in different groups of animals and effect of administration of the test composition/formulation.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected along with the present pharmaceutical carriers. Further, the responses may vary depending upon the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The present invention is directed to a pharmaceutical composition/formulation comprising a synergistic combination of OEA with other natural active ingredients which effectively reduces body weight. Additionally, the pharmaceutical composition/formulation improves liver functions by significantly reducing the level of triglyceride and cholesterol in liver and also reduces steatosis, irrespective of the etiology of the pathology. Further, it can be administered to prevent NAFLD and NASH in a subject suffering from metabolic syndrome and/or obesity and/or diabetes.

The inventors carried out extensive research studies along with pre-clinical studies and found that the combination of OEA with other natural ingredients of the present invention is extremely effective in the treatment of obesity and its related disorder associated with fat metabolism like NAFLD and NASH by significantly reducing tri-glyceride and cholesterol levels in serum and liver.

Within the scope of the present invention, it has now been found that the synergistic combination of OEA with other natural active ingredients have surprising and particularly advantageous properties. This makes them particularly suitable for treating and/or preventing (including preventing, slowing, delaying and/or reversing the progression or reducing the occurrence or delaying the onset) NAFLD including hepatic steatosis, NASH and/or liver fibrosis, and/or diseases related therewith and for preventing liver cirrhosis (irreversible advanced scarring of the liver), and/or hepatocellular carcinomas.

An objective of the present invention is to provide a pharmaceutical composition/formulation comprising a synergistic combination of OEA with other natural active ingredients which effectively reduces body weight.

In an embodiment, the present invention provides a pharmaceutical composition/formulation comprising a synergistic combination of OEA with other natural active ingredients for use in the treatment and/or prevention of obesity and its related associated with fat metabolism like NASH, NAFLD.

The present invention also provides a pharmaceutical composition/formulation comprising a synergistic combination of OEA with other natural active ingredients for reducing tri-glycerides and cholesterol levels in serum and liver.

The present invention further provides a pharmaceutical composition/formulation comprising a synergistic combination of OEA with other natural active ingredients for treating, delaying, slowing the progression of and/or preventing fatty liver diseases resulting from obesity including, but not limited to, alcoholic simple fatty liver, alcoholic steatohepatitis (ASH), alcoholic hepatic fibrosis, alcoholic cirrhosis, NAFLD, nonalcoholic simple fatty liver, NASH, nonalcoholic hepatic fibrosis and nonalcoholic cirrhosis.

The composition/formulation of the present invention can also reduce body weight and alter fat metabolism.

Another objective of the present invention is to provide a composition/formulation comprising a synergistic combination of OEA with natural active ingredients. The natural active ingredients can be selected from natural BAIBA, natural FAAH Inhibitor, natural alpha-glucosidase inhibitor, natural anti-oxidant or combinations thereof.

In aspect, the present invention provides a composition/formulation for treatment of obesity and its related disorder associated with fat metabolism, wherein said composition/formulation comprises a synergistic combination of:
(a) Oleoylethanolamide (OEA),
(b) Natural β-aminoisobutyric acid (BAIBA),
(c) Natural anti-oxidant and
(d) Optionally one or more other natural active ingredients selected from:
  (i) Natural Fatty Acid Amine Hydrolase Inhibitor (FAAH Inhibitor),
  (ii) Natural Alpha-glucosidase inhibitor, Accordingly, the main object of the present invention is to provide a pharmaceutical composition/formulation comprising a synergistic combination of OEA with natural BAIBA and/or natural anti-oxidant. In one aspect, the composition/formulation may optionally comprise Natural Alpha-glucosidase inhibitor and/or naturally occurring FAAH Inhibitor.

In the prior arts, it is known that OEA plays an important regulatory role in lipid metabolism and can enhance fatty acid oxidation in primary cultured skeletal muscle cells, liver cells and cardiac myocytes. Animal study confirms that OEA regulates fatty acid metabolism by activating PPAR-α. Obesity and insulin resistance are often accompanied by lipid metabolic disorders, which are turned out to be the main cause of NAFLD. OEA, an endogenous PPAR-α agonist, has a beneficial effect on HFD-induced NAFLD in rats via promoting fatty acid b-oxidation, and inhibiting de novo lipogenesis. In the prior arts, OEA was considered a better regulator for the treatment of obesity, atherosclerosis and other metabolic diseases. However, the effects of composition/formulation of the present invention comprising a synergistic combination of OEA with other natural ingredients to improve in the treatment of diet induced obesity and fatty liver diseases resulting from obesity have not been reported. This synergistic combination of the present invention plays a major role for treatment of obesity which is often accompanied by lipid metabolic disorders, and turn out to be the main cause of NAFLD. The combination of OEA with other natural active ingredients is able to provide a safe pharmaceutical composition/formulation with enhanced or synergistic effects compared to OEA alone in the treatment of diet induced obesity and fatty liver diseases resulting from obesity.

The composition/formulation of the present invention, containing OEA, natural BAIBA, natural anti-oxidant along with other natural ingredients like natural alpha-glucosidase inhibitor helps in the treatment of obese/overweight people with diabetes.

The side-effects of using synthetic ingredients (like chemically synthesized FAAH inhibitor) in pharmaceutical compositions are well-known. The composition/formulation of the present invention comprises natural FAAH inhibitors which inhibit degradation of OEA and increase the level of OEA in the body without any side effects.

In a preferred aspect, the ratio of OEA:natural BAIBA: natural anti-oxidant is in a range of 15-55:2-61:23-41. In a more preferred aspect, the ratio of OEA:natural BAIBA: natural anti-oxidant is 55:2:41.

The pharmaceutical composition/formulation of the present invention comprises OEA, wherein the amount of OEA in the pharmaceutical composition/formulation of the present invention ranges from 10% by wt. to 70% by wt. of the composition/formulation. In an embodiment, the amount of OEA ranges from 20% by wt. to 70% by wt. In yet another embodiment, the amount of OEA ranges from 30% by wt. to 70% by wt. In yet another embodiment, the amount of OEA ranges from 40% by wt. to 70% by wt. In yet another embodiment, the amount of OEA ranges from 50% by wt. to 70% by wt. In yet another embodiment, the amount of OEA ranges from 60% by wt. to 70% by wt.

In a preferred embodiment, the pharmaceutical composition/formulation of the present invention comprises OEA, wherein the amount of OEA in the pharmaceutical composition/formulation ranges from 100 mg to 1000 mg per unit dose.

The pharmaceutical composition/formulation of the present invention comprises natural BAIBA selected from amino acids such as valine, isoleucine or the like. The amount of natural BAIBA in the pharmaceutical composition/formulation of the present invention ranges from 2% by wt. to 60% by wt. of the composition/formulation. In an embodiment, the amount of natural BAIBA ranges from 5% by wt. to 60% by wt. In yet another embodiment, the amount of natural BAIBA ranges from 10% by wt. to 60% by wt. In yet another embodiment, the amount of natural BAIBA ranges from 20% by wt. to 60% by wt. In yet even another embodiment, the amount of natural BAIBA ranges from 30% by wt. to 60% by wt. In yet a further embodiment, the amount of natural BAIBA ranges from 40% by wt. to 60% by wt. In yet a further embodiment, the amount of natural BAIBA ranges from 50% by wt. to 60% by wt.

In a preferred embodiment, the pharmaceutical composition/formulation of the present invention comprises natural BAIBA selected from valine, isoleucine or the like, wherein the amount of natural BAIBA in the pharmaceutical composition/formulation ranges from 10 mg to 3000 mg per unit dose.

The pharmaceutical composition/formulation of the present invention comprises natural anti-oxidant selected from vitamin E, glutathione, selenium, pantethine, fucoxanthin or the like. The amount of natural anti-oxidant in the pharmaceutical composition/formulation of the present invention ranges from 20% by wt. to 35% by wt. of the composition/formulation. In an embodiment, the amount of natural anti-oxidant ranges from 25% by wt. to 35% by wt. In another embodiment, the amount of natural anti-oxidant ranges from 30% by wt. to 35% by wt.

In a preferred embodiment, the pharmaceutical composition/formulation of the present invention comprises natural anti-oxidant selected from selenium, glutathione, vitamin E, pantethine, fucoxanthin or the like, wherein the amount of natural anti-oxidant in the pharmaceutical composition/formulation ranges from 0.1 mg to 500 mg per unit dose.

In even another aspect, the pharmaceutical composition/formulation of the present invention comprises a synergistic combination of OEA, Valine, Pantethine and pharmaceutically acceptable excipients.

The pharmaceutical composition/formulation of the present invention optionally comprises other ingredients selected from natural alpha-glucosidase inhibitor or naturally occurring FAAH Inhibitor or combination thereof.

The pharmaceutical composition/formulation of the present invention further comprises natural alpha-glucosidase inhibitor such as 1-deoxynojirimycin which is derived from mulberry leaves. The amount of natural alpha-glucosidase inhibitor in the pharmaceutical composition/formulation of the present invention ranges from 0.5% by wt. to 1.5% by wt. of the composition/formulation.

In a preferred embodiment, the pharmaceutical composition/formulation of the invention comprises natural alpha-glucosidase inhibitor such as 1-deoxynojirimycin, wherein the amount of natural alpha-glucosidase inhibitor in the pharmaceutical composition/formulation ranges from 1 mg to 40 mg per unit dose.

The pharmaceutical composition/formulation of the invention comprises natural FAAH Inhibitors selected from Quercetin, Myricetin, Isorhamnetin, Kaempferol, Pristimerin, Curcumin, Biochanin A, Genistein, Daidzein or the like. The amount of natural FAAH Inhibitor in the pharmaceutical composition/formulation of the present invention ranges from 0.5% by wt. to 25% by wt. of the composition/formulation.

In a preferred embodiment, the pharmaceutical composition/formulation of the invention comprises natural FAAH Inhibitor selected from Quercetin, Myricetin, Isorhamnetin, Kaempferol, Pristimerin, Curcumin, Biochanin A, Genistein, Daidzein or the like, wherein the amount of natural FAAH Inhibitor in the pharmaceutical composition/formulation ranges from 1 mg to 100 mg per unit dose.

The pharmaceutical composition/formulation of the present invention can be formulated as tablets, capsules, granules, powder, sachets, suspension, solution, modified release formulations, topical formulations, etc. The formulations of the present invention comprise suitable excipients such as diluents, disintegrants, binders, solubilizing agent, lubricants, glidants, solvents etc.

In a preferred embodiment, the pharmaceutical composition/formulation according to the present invention can be formulated for oral administration. For oral administration, the solid pharmaceutical compositions can be in the form of, but not limited to, tablets, capsules, pills, hard capsules filled with liquids or solids, soft capsules, powders or granules, sachet, etc. The compositions may further comprise pharmaceutically acceptable excipients. The preferred excipients are selected from diluent, disintegrant, binder, glidant etc.

The diluents are selected from Microcrystalline cellulose, lactose (anhydrous/monohydrate/spray dried), starch, cellulose powder, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, compressible sugar, confectioner's sugar, corn starch, pregelatinized starch, dextrates, dextrin, dextrose, erythritol, ethylcellulose, fructose, fumaric acid, glyceryl palmitostearate, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, sterilizable maize, sucrose, sugar spheres, sulfobutylether β-cyclodextrin, talc, tragacanth, trehalose, xylitol or the like. The amount of diluent in the pharmaceutical composition/formulation of the present invention ranges from 1% by wt. to 30% by wt. of the composition/formulation.

The binder is selected from Hypromellose, starch, acacia, agar, alginic acid, calcium carbonate, calcium lactate, carbomers, carboxymethylcellulose sodium, carrageenan, cellulose acetate phthalate, ceratonia, chitosan, copovidone, corn starch, pregelatinized starch, cottonseed oil, dextrates, dextrin, dextrose, ethylcellulose, gelatin, glyceryl behenate, guar gum, hydrogenated vegetable oil type I, hydroxyethyl cellulose, hydroxyethylmethyl cellulose, hydroxypropyl cellulose, inulin, lactose, liquid glucose, low-substituted Hypromellose, magnesium aluminum silicate, maltodextrin, maltose, methylcellulose, microcrystalline cellulose, pectin, poloxamer, polycarbophil, polydextrose, polyethylene oxide, polymethacrylates, povidone, sodium alginate, stearic acid, sucrose, sunflower oil, tricaprylin, vitamin E polyethylene glycol succinate, zein or the like. The amount of binder in the pharmaceutical composition/formulation of the present invention ranges from 0.5% by wt. to 1.5% by wt. of the composition/formulation.

The lubricant is selected from magnesium stearate, zinc stearate, calcium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition/formulation of the present invention ranges from 0.5% by wt. to 5% by wt. of the composition/formulation.

The glidant is selected from colloidal silicon dioxide, talc, calcium phosphate tribasic, cellulose powdered, hydrophobic colloidal silica, magnesium oxide, magnesium silicate, magnesium trisilicate, silicon dioxide or the like. The amount of Glidant in the pharmaceutical composition/formulation of the present invention ranges from 1% by wt. to 25% by wt. of the composition/formulation.

The solvent is selected from water, alcohol, isopropyl alcohol, propylene glycol, almond oil, benzyl alcohol, benzyl benzoate, butylene glycol, carbon dioxide, castor oil, corn oil (maize), cottonseed oil, dibutyl phthalate, diethyl phthalate, dimethyl ether, albumin, dimethyl phthalate, dimethyl sulfoxide, dimethylacetamide, ethyl acetate, ethyl lactate, ethyl oleate, glycerin, glycofurol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl 35 castor oil, propylene carbonate, pyrrolidone, safflower oil, sesame oil, soybean oil, sunflower oil, triacetin, tricaprylin, triethanolamine, triethyl citrate, triolein, water-miscible solvents or the like. The amount of solvent in the pharmaceutical composition/formulation of the present invention is used in a quantity sufficient to 100% by wt. of the composition/formulation.

Developing pharmaceutical compositions or formulations wherein one or more ingredients are obtained from natural sources, like BAIBA, anti-oxidant, Alpha-glucosidase inhibitor and FAAH inhibitor poses challenge for the formulator. Such challenges are with respect to providing suitable size dosage form, yet containing the effective amount of the active ingredients. Challenges are also with respect to providing stable formulations, yet retaining the desirable pharmacokinetic properties. As per available information in public domain, till date, combination of OEA with natural BAIBA and natural anti-oxidant and/or natural Alpha-glucosidase inhibitor and/or natural FAAH inhibitor is not known. The present invention provides stable and therapeutically effective composition/formulation comprising OEA, natural BAIBA, natural anti-oxidant and optionally comprising natural Alpha-glucosidase inhibitor, natural FAAH inhibitor.

Some of the preferred composition/formulations of the present invention are as follows:

Composition/Formulation 1

| S. No. | Ingredient | Amount (% w/w) |
| --- | --- | --- |
| 1. | OEA | 10-70% |
| 2. | Natural BAIBA | 2-60% |
| 3. | Natural anti-oxidant | 20-35% |

Composition/Formulation 2

| S. No. | Ingredient | Amount (% w/w) |
| --- | --- | --- |
| 1. | OEA | 10-70% |
| 2. | Natural BAIBA | 2-60% |
| 3. | Natural anti-oxidant | 20-35% |
| 4. | Natural FAAH Inhibitor | 0.5-25% |

Composition/Formulation 3

| S. No. | Ingredient | Amount (% w/w) |
| --- | --- | --- |
| 1. | OEA | 10-70% |
| 2. | Natural BAIBA | 2-60% |
| 3. | Natural anti-oxidant | 20-35% |
| 4. | Natural alpha-glucosidase inhibitor | 0.5-1.5% |

Composition/Formulation 4

| S. No. | Ingredient | Amount (% w/w) |
| --- | --- | --- |
| 1. | OEA | 10-70% |
| 2. | Natural BAIBA | 2-60% |
| 3. | Natural anti-oxidant | 20-35% |
| 4. | Natural FAAH Inhibitor | 0.5-25% |
| 5. | Natural alpha-glucosidase inhibitor | 0.5-1.5% |

General Process for Preparation of the Composition/Formulation of the Present Invention 1. Accurately weight all of the material in separate containers.
2. Sift previously weighed OEA, natural anti-oxidant, natural BAIBA, diluent(s) and glidant(s) through sieve #40.
3. Mix content of step 2 in rapid mixer granulator with impeller of slow speed.
4. Binder solution Preparation: In a separate container, weigh a binding agent(s) and dissolve it into solvent(s) to get a clear transparent solution.

5. Add binder solution to step 3 in RMG at slow speed of impeller.
6. Sift and dry the obtained granulated wet mass in a Fluid bed dryer at 50° C.+5° C. until the level of dryness (LOD) of the blend is reduced to less than 1.5% w/w.
7. Sift semi dried granules through sieve #18 and sieve #24.
8. Sift previously weighed lubricant(s) or glidant(s) separately through sieve #40 and mix with Step-7.
9. Fill and seal the blend with HPMC capsule shells.
10. Transfer the filled capsules into the hopper of polishing and visual inspection machine to remove the debris of powder sticking with the capsule shells.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention. For the experiments, OEA and natural anti-oxidant were obtained from Wuxi Cima Science Co., Ltd No. 288 Shibawan Road Wuxi 214064 Jiangsu, China; Natural BAIBA was procured from Shantou Jiahe Biologic Technology Co., Ltd. Address: No. 4 Lane 1 Xigang Road, Shantou, 515021, P.R. China; 1-deoxynojirimycin (DNJ) derived from mulberry leaves obtained from Bio-gen Extracts Pvt. Ltd, No. 39/2, 3rd Floor, 8th Mile, T. Dasarahalli, Tumkur Road, Bengaluru—560057 and Natural FAAH Inhibitors were obtained from Navpad Trade Impex, Office No. 215, Sai Chamber, Near Bus Depot, Santacruz (East), Mumbai—400055.

Example 1

| Sr. No. | Ingredients | % w/w |
|---|---|---|
| | Intragranular Ingredients | |
| 1 | Oleoylethanolamide (OEA) | 44.44 |
| 2 | L-Valine | 2.22 |
| 3 | Microcrystalline Cellulose pH 101 | 29.44 |
| 4 | Colloidal silicone dioxide | 17.78 |
| | Binder Solution | |
| 5 | HPMC 5 cps | 0.56 |
| 6 | Isopropyl alcohol | q.s. |
| 7 | Methylene dichloride | q.s. |
| | Extragranular Ingredients | |
| 8 | Colloidal silicone dioxide | 2.78 |
| 9 | Magnesium Stearate | 2.78 |
| | Net Fill Content | 100.00 |

Example 2

| Sr. No. | Ingredients | % w/w |
|---|---|---|
| | Intragranular Ingredients | |
| 1 | Oleoylethanolamide | 40.00 |
| 2 | Isoleucine | 45.00 |
| 3 | Dicalcium Phosphate | 8.50 |
| 4 | Colloidal silicone dioxide | 4.00 |
| | Binder Solution | |
| 5 | PVP-K 30 | 0.50 |
| 6 | Isopropyl alcohol | q.s. |
| 7 | Methylene dichloride | q.s. |
| | Extragranular Ingredients | |
| 8 | Colloidal silicone dioxide | 1.00 |
| 9 | Talc | 1.00 |
| | Net Fill Content | 100.00 |

Example 3

| Sr. No. | Ingredients | % w/w |
|---|---|---|
| | Intragranular Ingredients | |
| 1 | Oleoylethanolamide | 43.48 |
| 2 | Fucoxanthin | 21.74 |
| 3 | Isoleucine | 10.87 |
| 4 | Dicalcium Phosphate | 9.24 |
| 5 | Colloidal silicone dioxide | 8.70 |
| | Binder Solution | |
| 5 | PVP-K 30 | 0.54 |
| 6 | Isopropyl alcohol | q.s. |
| 7 | Methylene dichloride | q.s. |
| | Extragranular Ingredients | |
| 8 | Colloidal silicone dioxide | 2.72 |
| 9 | Magnesium Stearate | 2.72 |
| | Net Fill Content | 100.00 |

Example 4

| Sr. No. | Ingredients | % w/w |
|---|---|---|
| | Intragranular Ingredients | |
| 1 | Oleoylethanolamide | 50.00 |
| 2 | L-Valine | 2.50 |
| 3 | Daidzein | 12.50 |
| 4 | Lactose Anhydrous | 18.13 |
| 5 | Colloidal silicone dioxide | 10.00 |
| | Binder Solution | |
| 6 | Ethyl cellulose | 0.63 |
| 7 | Isopropyl alcohol | q.s. |
| 8 | Methylene dichloride | q.s. |
| | Extragranular Ingredients | |
| 9 | Zinc Stearate | 3.13 |
| 10 | Talc | 3.13 |
| | Net Fill Content | 100.00 |

Example 5

| Sr. No. | Ingredients | % w/w |
|---|---|---|
| | Intragranular Ingredients | |
| 1 | Oleoylethanolamide | 57.14 |
| 2 | L-Valine | 2.86 |
| 3 | Genistein | 1.14 |
| 4 | Mannitol | 20.29 |
| 5 | Colloidal silicone dioxide | 11.43 |
| | Binder Solution | |
| 6 | Starch | 1.43 |
| 7 | Isopropyl alcohol | q.s. |
| 8 | Purified Water | q.s. |
| | Extragranular Ingredients | |
| 9 | Magnesium Stearate | 2.86 |
| 10 | Colloidal silicone dioxide | 2.86 |
| | Net Fill Content | 100.00 |

Example 6

| Sr. No. | Ingredients | % w/w |
|---|---|---|
| | Intragranular Ingredients | |
| 1 | Oleoylethanolamide | 50.00 |
| 2 | L-Valine | 2.50 |
| 3 | Myricetin | 25.00 |
| 4 | Microcrystalline Cellulose pH 101 | 6.25 |
| 5 | Colloidal silicone dioxide | 10.00 |
| | Binder Solution | |
| 6 | HPMC 5 cps | 1.25 |
| 7 | Isopropyl alcohol | q.s. |
| 8 | Methylene dichloride | q.s. |
| | Extragranular Ingredients | |
| 9 | Talc | 2.50 |
| 10 | Colloidal silicone dioxide | 2.50 |
| | Net Fill Content | 100.00 |

Example 7

| Sr. No. | Ingredients | % w/w |
|---|---|---|
| | Intragranular Ingredients | |
| 1 | Oleoylethanolamide | 57.14 |
| 2 | L-Valine | 2.86 |
| 3 | Lactose Monohydrate | 14.29 |
| 4 | Colloidal silicone dioxide | 17.14 |
| | Binder Solution | |
| 5 | PVP K-30 | 1.43 |
| 6 | DNJ (Mulberry leaf extract) | 1.14 |
| 7 | Isopropyl alcohol | q.s. |
| 8 | Methylene dichloride | q.s. |
| | Extragranular Ingredients | |
| 9 | Zinc stearate | 3.00 |
| 10 | Talc | 3.00 |
| | Net Fill Content | 100.00 |

Example 8

| Sr. No. | Ingredients | % w/w |
|---|---|---|
| | Intragranular Ingredients | |
| 1 | Oleoylethanolamide | 50.00 |
| 2 | L-Valine | 2.50 |
| 3 | Daidzein | 12.50 |
| 4 | Lactose Monohydrate | 12.50 |
| 5 | Colloidal silicone dioxide | 15.00 |
| | Binder Solution | |
| 6 | PVP K-30 | 1.25 |
| 7 | DNJ (Mulberry leaf extract) | 1.00 |
| 8 | Isopropyl alcohol | q.s. |
| 9 | Methylene dichloride | q.s. |
| | Extragranular Ingredients | |
| 10 | Zinc stearate | 2.63 |
| 11 | Talc | 2.63 |
| | Net Fill Content | 100.00 |

Example 9

| Sr. No. | Ingredients | % w/w |
|---|---|---|
| | Intragranular Ingredients | |
| 1 | Oleoylethanolamide | 50.00 |
| 2 | L-Valine | 2.50 |
| 3 | Myricetin | 25.00 |
| 4 | Dicalcium Phosphate | 7.75 |
| 5 | Colloidal silicone dioxide | 10.00 |
| | Binder Solution | |
| 6 | HPMC 5 cps | 1.25 |
| 7 | DNJ (Mulberry leaf extract) | 1.00 |
| 8 | Isopropyl alcohol | q.s. |
| 9 | Methylene dichloride | q.s. |
| | Extragranular Ingredients | |
| 10 | Magnesium stearate | 1.25 |
| 11 | Colloidal silicone dioxide | 1.25 |
| | Net Fill Content | 100.00 |

Example 10

| Sr. No. | Ingredients | % w/w |
|---|---|---|
| | Intragranular Ingredients | |
| 1 | Oleoylethanolamide | 40.00 |
| 2 | Valine | 2.00 |
| 3 | Daidzein | 10.00 |
| 4 | Pantethine (Diluted) | 30.00 |
| 5 | Dicalcium Phosphate | 7.00 |
| 6 | Colloidal silicone dioxide | 8.00 |
| | Binder Solution | |
| 7 | HPMC 5 cps | 1.00 |
| 8 | Isopropyl alcohol | q.s. |
| 9 | Methylene dichloride | q.s. |

-continued

| Sr. No. | Ingredients | % w/w |
|---|---|---|
| | Extragranular Ingredients | |
| 10 | Magnesium stearate | 1.00 |
| 11 | Colloidal silicone dioxide | 1.00 |
| | Net Fill Content | 100.00 |

Example 11

| Sr. No. | Ingredients | % w/w |
|---|---|---|
| | Intragranular Ingredients | |
| 1 | Oleoylethanolamide | 44.44 |
| 2 | L-Valine | 2.22 |
| 3 | Genistein | 0.89 |
| 4 | Pantethine (Diluted) | 33.33 |
| 5 | Dicalcium Phosphate | 6.89 |
| 6 | Colloidal silicone dioxide | 8.89 |
| | Binder Solution | |
| 7 | PVP K-30 | 1.11 |
| 8 | Isopropyl alcohol | q.s. |
| 9 | Methylene dichloride | q.s. |
| | Extragranular Ingredients | |
| 10 | Magnesium stearate | 1.11 |
| 11 | Colloidal silicone dioxide | 1.11 |
| | Net Fill Content | 100.00 |

Example 12

| Sr. No. | Ingredients | % w/w |
|---|---|---|
| | Intragranular Ingredients | |
| 1 | Oleoylethanolamide | 44.44 |
| 2 | L-Valine | 2.22 |
| 3 | Pantethine (Diluted) | 33.33 |
| 4 | Dicalcium Phosphate | 6.89 |
| 5 | Colloidal silicone dioxide | 8.89 |
| | Binder Solution | |
| 6 | HPMC 5 cps | 1.11 |
| 7 | DNJ (Mulberry leaf extract) | 0.89 |
| 8 | Isopropyl alcohol | q.s. |
| 9 | Methylene dichloride | q.s. |
| | Extragranular Ingredients | |
| 10 | Magnesium stearate | 1.11 |
| 11 | Colloidal silicone dioxide | 1.11 |
| | Net Fill Content | 100.00 |

Example 13

| Sr. No. | Ingredients | % w/w |
|---|---|---|
| | Intragranular Ingredients | |
| 1 | Oleoylethanolamide | 40.00 |
| 2 | L-Valine | 2.00 |

-continued

| Sr. No. | Ingredients | % w/w |
|---|---|---|
| 3 | Pantethine (Diluted) | 30.00 |
| 4 | Daidzein | 10.00 |
| 5 | Microcrystalline cellulose pH 101 | 6.20 |
| 6 | Colloidal silicone dioxide | 8.00 |
| | Binder Solution | |
| 7 | PVP K-30 | 1.00 |
| 8 | DNJ (Mulberry leaf extract) | 0.80 |
| 9 | Isopropyl alcohol | q.s. |
| 10 | Methylene dichloride | q.s. |
| | Extragranular Ingredients | |
| 11 | Zinc stearate | 1.00 |
| 12 | Talc | 1.00 |
| | Net Fill Content | 100.00 |

Example 14

| Sr. No. | Ingredients | % w/w |
|---|---|---|
| | Intragranular Ingredients | |
| 1 | Oleoylethanolamide | 44.44 |
| 2 | L-Valine | 2.22 |
| 3 | Pantethine (Diluted) | 33.33 |
| 4 | Microcrystalline cellulose pH 101 | 6.00 |
| 5 | Colloidal silicone dioxide | 8.89 |
| | Binder Solution | |
| 6 | PVP K-30 | 1.11 |
| 7 | DNJ (Mulberry leaf extract) | 0.89 |
| 8 | Genistein | 0.89 |
| 9 | Isopropyl alcohol | q.s. |
| 10 | Methylene dichloride | q.s. |
| | Extragranular Ingredients | |
| 11 | Zinc stearate | 1.11 |
| 12 | Talc | 1.11 |
| | Net Fill Content | 100.00 |

Example 15

| Sr. No. | Ingredients | % w/w |
|---|---|---|
| | Intragranular Ingredients | |
| 1 | Oleoylethanolamide | 42.55 |
| 2 | Pantethine (Diluted) | 31.91 |
| 3 | L-Valine | 2.13 |
| 4 | Microcrystalline cellulose pH 101 | 9.04 |
| 5 | Colloidal Silicone dioxide | 8.51 |
| | Binder Solution | |
| 6 | Hypromellose 5 cps | 0.53 |
| 7 | Isopropyl alcohol | q.s. |
| 8 | Dichloromethane | q.s. |
| | Extragranular Ingredients | |
| 9 | Colloidal silicone dioxide | 2.66 |
| 10 | Magnesium Stearate | 2.66 |
| | Net Fill Content | 100.00 |

Example 16

| Sr. No. | Ingredients | % w/w |
|---|---|---|
| | Intragranular Ingredients | |
| 1 | Oleoylethanolamide | 61.54 |
| 2 | Pantethine (Diluted) | 23.08 |
| 3 | L-Valine | 7.69 |
| 4 | Microcrystalline cellulose pH 101 | 1.85 |
| 5 | Colloidal Silicone dioxide | 3.08 |
| | Binder Solution | |
| 10 | Hypromellose 5 cps | 0.62 |
| 11 | Isopropyl alcohol | q.s. |
| 12 | Dichloromethane | q.s. |
| | Extragranular Ingredients | |
| 14 | Colloidal silicone dioxide | 1.08 |
| 15 | Magnesium Stearate | 1.08 |
| | Net Fill Content | 100.00 |

Example 17

| Sr. No. | Ingredients | % w/w |
|---|---|---|
| | Intragranular Ingredients | |
| 1 | Oleoylethanolamide | 14.29 |
| 2 | Pantethine (Diluted) | 21.43 |
| 3 | L-Valine | 57.14 |
| 4 | Microcrystalline cellulose pH 101 | 1.57 |
| 5 | Colloidal Silicone dioxide | 3.57 |
| | Binder Solution | |
| 8 | Hypromellose 5 cps | 0.57 |
| 9 | Isopropyl alcohol | q.s. |
| 10 | Dichloromethane | q.s. |
| | Extragranular Ingredients | |
| 14 | Colloidal silicone dioxide | 0.71 |
| 15 | Magnesium Stearate | 0.71 |
| | Net Fill Content | 100.00 |

Example 18: Stability Study and Dissolution Study of Formulations of Example 1

Stability Condition: Accelerated Stability Testing: 40° C., 75% RH

| Sr. No. | Test | Specification | Initial | 1 Months | 3 Months | 6 Months |
|---|---|---|---|---|---|---|
| 1 | Description | White to off white granular powder filled in size "0" capsules | Complies | Complies | Complies | Complies |
| 2 | Average weight of capsules | 550 ± 7.5% | 551.5 mg | 550.9 mg | 552.5 mg | 550.7 mg |
| 3 | Net fill content | 450 ± 7.5% | 450.5 mg | 452.8 mg | 454.8 mg | 452.7 mg |
| 4 | Disintegration time | Not More Than 30 minutes | 7-8 minutes | 6-8 minutes | 7-8 minutes | 6-7 minutes |
| 5 | Assay | | | | | |
| 5.1 | Assay of OEA | Between 90.0% and 110.0% of LC | 99.5% | 100.7% | 99.6% | 98.9% |
| 5.2 | Assay of L-Valine | Between 90.0% and 110.0% of LC | 98.6% | 99.5% | 100.2% | 97.6% |
| 6 | Dissolution | | | | | |
| 6.1 | Dissolution of OEA | Not less than 75% of LC | 89.5% | 87.7% | 88.6% | 88.9% |
| 6.2 | Dissolution of L-Valine | Not less than 75% of LC | 83.6% | 82.5% | 89.2% | 84.6% |

Example 19: Stability Study and Dissolution Study of Formulations of Example 12

Stability Condition: Accelerated Stability Testing: 40° C., 75% RH

| Sr. No. | Test | Specification | Initial | 1 Months | 3 Months | 6 Months |
|---|---|---|---|---|---|---|
| 1 | Description | White to off white granular powder filled in size "0" capsules | Complies | Complies | Complies | Complies |
| 2 | Average weight of capsules | 550 ± 7.5% | 553.7 mg | 552.7 mg | 553.8 mg | 554.8 mg |
| 3 | Net fill content | 450 ± 7.5% | 451.8 mg | 451.7 mg | 453.5 mg | 451.9 mg |
| 4 | Disintegration time | Not More Than 30 minutes | 7-8 minutes | 6-8 minutes | 7-8 minutes | 6-7 minutes |

-continued

| Sr. No. | Test | Specification | Initial | 1 Months | 3 Months | 6 Months |
|---|---|---|---|---|---|---|
| 5 | | Assay | | | | |
| 5.1 | Assay of OEA | Between 90.0% and 110.0% of LC | 98.1% | 99.6% | 97.5% | 97.1% |
| 5.2 | Assay of Pantethine (50%) | Between 90.0% and 110.0% of LC | 97.3% | 97.6% | 97.3% | 98.1% |
| 5.3 | Assay of L-Valine | Between 90.0% and 110.0% of LC | 97.4% | 99.3% | 100.0% | 98.7% |
| 5.4 | Assay of Mulberry Leaf Extract | Between 90.0% and 110.0% of LC | 91.4% | 92.3% | 93.1% | 92.9% |
| 6 | Dissolution | | | | | |
| 6.1 | Assay of OEA | Not less than 75% of LC | 88.7% | 86.8% | 86.5% | 87.1% |
| 6.2 | Dissolution of Pantethine (50%) | Not less than 75% of LC | 81.9% | 80.1% | 84.5% | 85.7% |
| 6.3 | Dissolution of L-Valine | Not less than 75% of LC | 84.8% | 82.5% | 84.3% | 85.9% |
| 6.4 | Dissolution of Mulberry Leaf Extract | Not Less than 70% in 60 minutes | 89.2% | 85.1% | 83.3% | 81.5% |

Example 20: Stability Study and Dissolution Study of Formulations of Example 15

Stability Condition: Accelerated Stability Testing: 40° C., 75% RH

| Sr. No. | Test | Specification | Initial | 1 Months | 3 Months | 6 Months |
|---|---|---|---|---|---|---|
| 1 | Description | White to off white granular powder filled in size "0" capsules | Complies | Complies | Complies | Complies |
| 2 | Average weight of capsules | 570 ± 7.5% | 572.4 mg | 571.8 mg | 573.4 mg | 571.6 mg |
| 3 | Net fill content | 470 ± 7.5% | 471.4 mg | 473.7 mg | 475.9 mg | 471.4 mg |
| 4 | Disintegration time | Not More Than 30 minutes | 6-7 minutes | 6-8 minutes | 7-8 minutes | 6-7 minutes |
| 5 | Assay | | | | | |
| 5.1 | Assay of OEA | Between 90.0% and 110.0% of LC | 98.2% | 99.1% | 98.4% | 98.7% |
| 5.2 | Assay of Pantethine (Diluted) | Between 90.0% and 110.0% of LC | 97.1% | 98.0% | 98.1% | 97.0% |
| 5.3 | Assay of L-Valine | Between 90.0% and 110.0% of LC | 99.5% | 98.6% | 99.3% | 98.5% |
| 6 | Dissolution | | | | | |
| 6.1 | Dissolution of OEA | Not less than 75% of LC | 88.4% | 88.6% | 89.5% | 89.8% |
| 6.2 | Dissolution of Pantethine (Diluted) | Not less than 75% of LC | 81.1% | 80.3% | 82.1% | 85.4% |
| 6.3 | Dissolution of L-Valine | Not less than 75% of LC | 82.5% | 83.4% | 88.1% | 85.5% |

Example 21—Animal Study

Screening anti-obesity effect of synergistic combination or composition/formulation comprising OEA and other natural ingredients using High fat diet induced obesity model in rat. The following trials were carried out:

48 Male Wistar Rats (*Rat Rattus*) (6 per group) were maintained in animal house in a light/dark atmosphere based on a 12-hour cycle having temperature and relative humidity in the range of 18-29° C. and 30-70%, respectively. To maintain appropriate conditions, temperature and relative humidity were recorded three times daily. During complete experiment, animals were supplied with the standard certified rat pellet feed (manufactured by VRK Nutritional Solutions, Pune) and drinking water treated by the reverse osmosis ad libitum.

The composition of Normal pellet diet contained protein (18.1% w/w), fat (3.1% w/w), fiber (5.5% w/w), calcium (1.2% w/w), phosphorous (0.5% w/w), total ash (5.5% w/w), carbohydrate (63% w/w) and moisture (7% w/w).

The composition of high fat diet contained Normal pellet diet (36.5% w/w), Soybean powder (25% w/w), Cheese (31% w/w), Dalda Ghee (1% w/w), Mixture of Vitamins & Minerals (6% w/w), DL-methionine (0.3% w/w), Yeast powder (0.1% w/w), Sodium chloride (0.1% w/w) procured from local market.

In order to evaluate the anti-obesity effect, forty-eight (48) male rats were screened and divided into eight groups. For a comparative analysis, the groups were divided as follows: normal control, disease control, treatment groups with individual component, reference standard drug and test composition/formulation of the present invention. Table 1 provides the details of the various groups and treatments conducted in the trial.

TABLE 1

| S. No. | Group | No. of animals | Test drug (mg/kg, p.o.) |
|---|---|---|---|
| 1. | G1 (Normal control) | 6 | Normal Control |
| 2. | G2 (Disease control) | 6 | Disease Control |
| 3. | G3 (OEA) | 6 | OEA (41 mg/kg) |
| 4. | G4 (L-Valine) | 6 | L-Valine (2 mg/kg) |
| 5. | G5 (Pantethine) | 6 | Pantethine (31 mg/kg) |

TABLE 1-continued

| S. No. | Group | No. of animals | Test drug (mg/kg, p.o.) |
|---|---|---|---|
| 6. | G6 (OEA + L-Valine) | 6 | OEA (41 mg/kg) + L-Valine (2 mg/kg) (Example 1) |
| 7. | G7 [Test Composition (OEA + L-Valine + Pantethine)] | 6 | OEA (41 mg/kg) + L-Valine (2 mg/kg) + Pantethine (31 mg/kg) (Example 15) |
| 8. | G8 (Reference drug) | 6 | Reference standard (Orlistat 10 mg/kg) |

TABLE 2

| | | Body weight | |
|---|---|---|---|
| Group No. | Group ID | gm | % increase in body weight |
| G1 | Normal Control | 276.00 | 0.00 |
| G2 | Disease Control | 340.17 | 23.25 |
| G3 | OEA | 310.00 | 12.32 |
| G4 | L-Valine | 338.67 | 22.71 |
| G5 | Pantethine | 327.83 | 18.78 |
| G6 | OEA + L-Valine | 316.67 | 14.73 |
| G7 | OEA + L-Valine + Pantethine | 293.33 | 6.28 |
| G8 | Orlistat | 298.00 | 7.97 |

All above values are in mean

TABLE 3

| Group No. | Group ID | Triglyceride (mg/dl) | % Decrease | Total Cholesterol (mg/dl) | % Decrease | LDL (mg/dl) | % Decrease |
|---|---|---|---|---|---|---|---|
| G1 | Normal | 70.24 | — | 79.71 | — | 21.23 | — |
| G2 | Disease Control | 122.78 | — | 147.24 | — | 57.97 | — |
| G3 | OEA | 100.05 | 18.51 | 105.54 | 28.32 | 35.54 | 38.70 |
| G4 | L-Valine | 115.23 | 6.15 | 140.00 | 4.92 | 55.45 | 4.35 |
| G5 | Pantethine | 110.13 | 10.30 | 135.54 | 7.95 | 49.17 | 15.19 |
| G6 | OEA + L-Valine | 96.22 | 21.63 | 103.22 | 29.90 | 33.32 | 42.53 |
| G7 | OEA + L-Valine + Pantethine | 73.98 | 39.75 | 80.55 | 45.29 | 22.52 | 61.16 |
| G8 | Orlistat | 77.62 | 36.78 | 84.27 | 42.77 | 25.74 | 55.60 |

All above values are in mean

TABLE 4

| Group No. | Group ID | Triglyceride (mg/dl) | % Decrease | Total Cholesterol (mg/dl) | % Decrease |
|---|---|---|---|---|---|
| G1 | Normal Control | 40.23 | — | 56.21 | — |
| G2 | Disease Control | 83.00 | — | 90.25 | — |
| G3 | OEA | 59.98 | 27.74 | 74.12 | 17.87 |
| G4 | L-Valine | 80.02 | 3.59 | 85.23 | 5.56 |
| G5 | Pantethine | 75.22 | 9.38 | 82.41 | 8.68 |
| G6 | OEA + L-Valine | 55.33 | 33.34 | 68.32 | 24.30 |
| G7 | OEA + L-Valine + Pantethine | 43.84 | 47.18 | 57.22 | 36.60 |
| G8 | Orlistat | 44.82 | 46.00 | 60.33 | 33.15 |

All above values are in mean

Treatment Protocol:

The animals under consideration were examined for a study period of 12 weeks. Animals in group (G1) were given normal pellet diet, wherein the other groups were on high fat diet. After completion of study for 12 weeks, each group was analyzed in terms of the body weight and other evaluating parameters such as serum biochemistry (triglyceride, total cholesterol and low density lipoprotein cholesterol (LDL), analysis of liver homogenates and histopathology of liver.

Table 2 represents the analysis of body weight measured in different groups

Table 3 provides the summary of the results obtained in serum biochemistry in terms of the % decrease in triglyceride, total cholesterol and LDL.

Table 4 describes the summary of results obtained in liver biochemistry in terms of the % decrease in triglyceride and total cholesterol.

Interpretation and Inference:

Obesity is essentially due to an excessive accumulation of the fatty tissues which leads to many diseases, not limited to insulin resistance, diabetes, fatty liver disease, coronary artery disease, hypertension and polycystic ovary syndrome. In obese conditions, the level of total cholesterol, triglyceride and LDL-cholesterol reaches beyond the normal ranges in human beings. Similarly, high fat diet model in rat is universally accepted model to test the efficacy of the drug for the treatment of obesity. In the above experimental procedure, obesity was induced by administration of a high fat diet (HFD) for the period of 12 weeks. For comparison, the normal control group animals were given a normal pellet diet, whereas the remaining groups were fed with the HFD.

As a routine experiment, all animals' body weights were observed on weekly basis. Further, various serum biochemistry parameters such as Triglyceride, total cholesterol and LDL-cholesterol were analyzed at the end of the 12-week treatment period. In this regard, at the end of study period, all animals were euthanized and the liver was isolated. The liver homogenate of each individual animal was prepared and subjected for determination of the level of total cholesterol and Triglyceride. Further, part of the liver was used for histopathological investigation purpose.

Analysis of Body Weight

The primary observation during the experiment was monitoring the body weight of animals. Though the animals were tested weekly for the change in the body weight, an average body weight was measured at the end of 12 weeks, and is tabulated in the Table 2. It is evident that the average body weight of the disease control group (G2) was significantly higher (23.25%) in comparison to the normal group (G1). The test composition (G7) showed a tendency of reduced body gain, effectively due to the composition/formulation of the present invention. From the results mentioned in the Table 2 which elaborated a comparative study of the % increase in body weight in different groups of animals and effect of administration of the test composition/formulation, it is evident that the test composition effectively reduces weight gain in comparison to the other groups including the reference drug (FIG. 1).

Pathophysiology Study

At the end of the 12-week period there was a significant increase ($p<0.001$) in the level of total cholesterol, Triglyceride and LDL-cholesterol in serum in disease control group as compared to normal control group, which indicate that obesity was successfully induced in models during the study.

Figure 2:
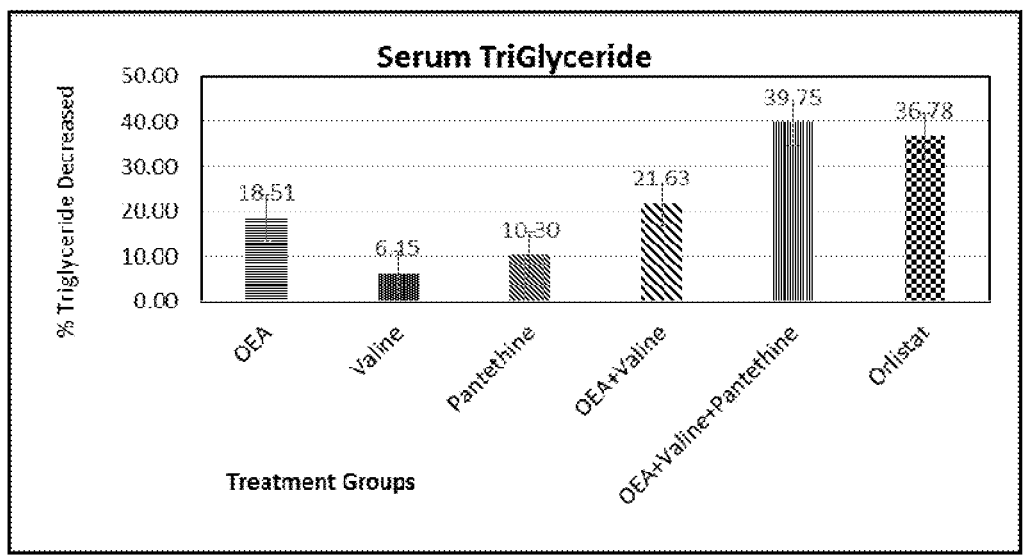
FIG. 2: A comparative study of the percentage decrease in serum triglycerides level in different groups of animals and effect of administration of the test composition/formulation.
Figure 3:
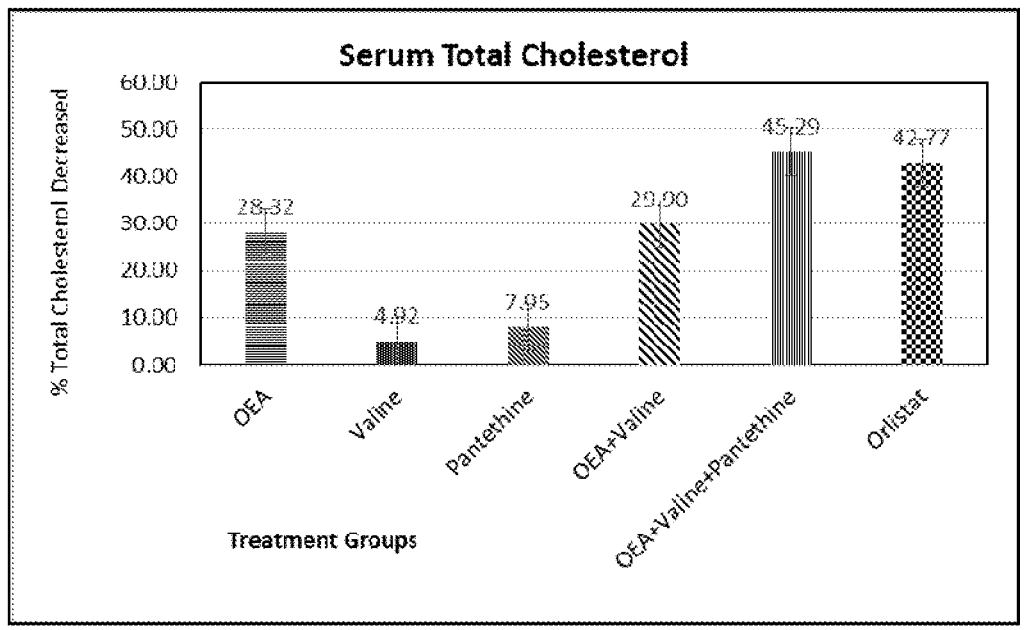
FIG. 3: A comparative study of the percentage decrease in serum total cholesterol level in different groups of animals and effect of administration of the test composition/formulation.
Figure 4:
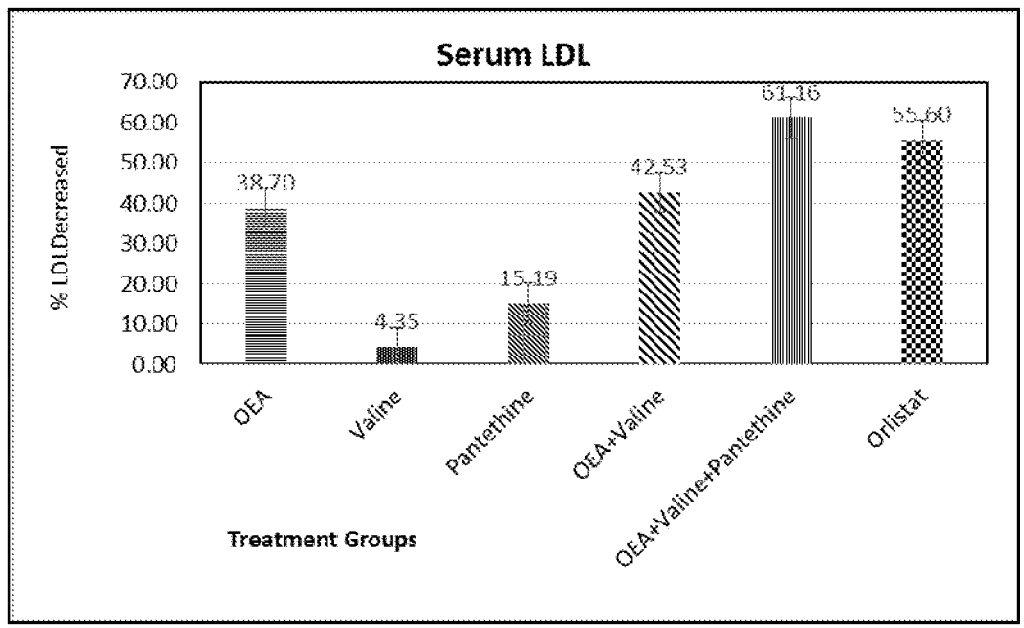
FIG. 4: A comparative study of the percentage decrease in serum LDL level in different groups of animals and effect of administration of the test composition/formulation.

From the results mentioned in the Table 3, there was a significant reduction ($p<0.001$) in the level of total cholesterol, Triglyceride and LDL-cholesterol in serum in case of treatment group providing test composition (G7) compared to disease control group (FIGS. 2-4). These results are indicative of the fact that the use of combination of test composition/formulation (G7) for treatment of obesity and related disorders in rats have grater efficacy than individual components as specified in groups G3-G6. The test composition also showed the better results compared to the reference drug as well.

Figure 5:
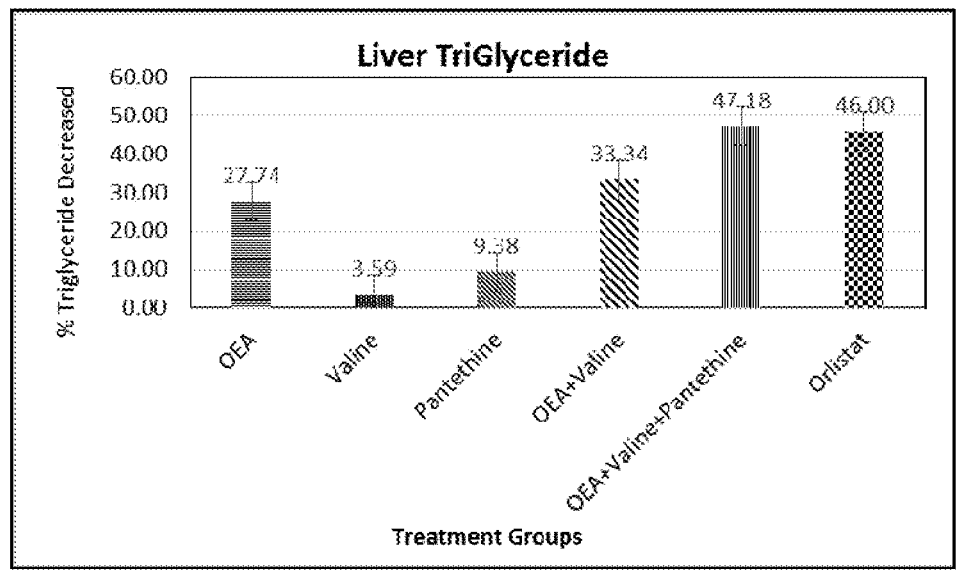
FIG. 5: A comparative study of the percentage decrease in liver triglycerides level in different groups of animals and effect of administration of the test composition/formulation.
Figure 6:
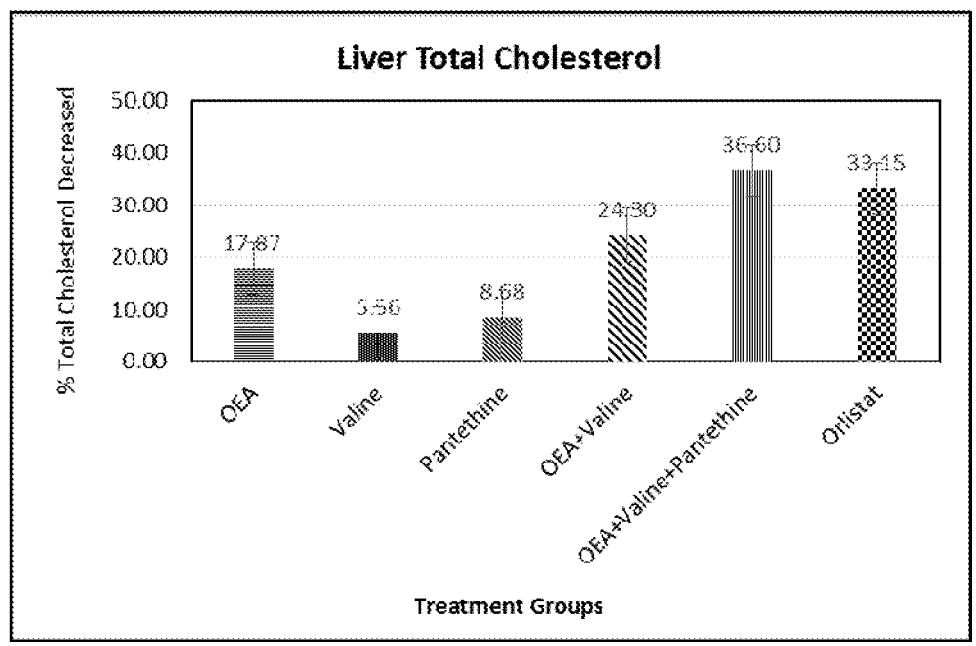
FIG. 6: A comparative study of the percentage decrease in total cholesterol level in liver in different groups of animals and effect of administration of the test composition/formulation.

Further, after 12 weeks of treatment, the level of total cholesterol and Triglyceride was also determined in the liver homogenate. As evidenced in the Table 4, there was a reduction in the level of Triglyceride and total cholesterol observed in liver homogenate in case of all treatment group (G3 to G8) as compared to disease control group (FIGS. 5-6). More particularly, it needs to be considered that there was a significant reduction ($p<0.001$) in the level of total cholesterol and Triglyceride in the liver in case of treatment group providing test composition (G7) compared to disease control group. This indicates that treatment by OEA combination was more effective in lowering level of total cholesterol and Triglyceride in liver as compared to individual components as specified in groups G3-G6. The test composition also showed the better results compared to the reference drug as well.

As evident from the data summarized in the Table 3, the % decrease in triglyceride, total cholesterol and LDL levels in serum have comparative differences in the measure parameters. The % decrease in triglyceride by individual effect of the drug administered in groups G3, G4, G5 and G6 were observed as 18.51, 6.15, 10.30 and 21.63 respectively whereas the test composition (G7) of the present invention showed better results having 39.75% decrease in triglyceride level. Further, the % decrease in total cholesterol by individual effect of the drug administered in groups G3, G4, G5 and G6 were observed as 28.32, 4.92, 7.95 and 29.90 respectively whereas the test composition (G7) of the present invention showed better results having 45.29% decrease in total cholesterol level. Similarly, the % decrease in LDL by individual effect of the drug administered in groups G3, G4, G5 and G6 were observed as 38.70, 4.35, 15.19 and 42.53 respectively whereas the test composition (G7) of the present invention showed better results having a 61.16% decrease in LDL level.

Similarly, it has been observed that in the case of histopathology of the liver, the level of steatosis was significantly lower in case of treatment group provided the test composition (G7).

As evident from the data summarized in the Table 4, the % decrease in triglyceride and total cholesterol levels in liver have comparative differences in the measure parameters. The % decrease in triglyceride by individual effect of the drug administered in groups G3, G4, G5 and G6 were observed as 27.74, 3.59, 9.38 and 33.34 respectively whereas the test composition (G7) of the present invention showed better results having a 47.18% decrease in triglyceride level. Further, the % decrease in total cholesterol by individual effect of the drug administered in groups G3, G4, G5 and G6 were observed as 17.87, 5.56, 8.68 and 24.30 respectively whereas the test composition (G7) of the present invention showed better results having a 36.60% decrease in total cholesterol level.

Among the treatment groups, test composition (G7) has been observed for exhibiting the highest anti-obesity activity in HFD-fed rats. The data evidencing the same has been summarized in Tables 2-4 and FIGS. 1-6. It is evident from the study that the test composition/formulation (G7) provides synergistic effect over individual components of the composition and from the reference drug and also plays an important role in anti-obesity activity in HFD-fed rats.

Moreover, there was no mortality observed in case of any of the group of animals, which indicate that the obesity not lead to death but it increases burden of morbidity in the animals.

CONCLUSION

Based on the experimental study conducted on animals, it can be concluded that the test composition of the present invention was found to be more effective and have synergistic effect when compared to the individual drug for treating HFD induced rats.

Based on the study, it has also been observed that the pharmaceutical composition/formulation of the present invention was safe and effective for reducing body weight, triglyceride and cholesterol levels, and thus decreasing the risk of obesity and its fat metabolism related disorders.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the res tills arc contemplated in accordance with the objects and practices of the present invention. It is intended, therefore, that the invention be defined by the scope of the claims which follow and that such claims be interpreted as broadly as is reasonable.

We claim:

1. A pharmaceutical composition comprising a combination of:
    Oleoylethanolamide (OEA) ranging from 10 to 70% by wt. of the composition;
    naturally occurring β-aminoisobutyric acid (BAIBA) ranging from 2 to 60% by wt. of the composition, and selected from the group consisting of valine, iso-leucine and combinations thereof; and
    natural anti-oxidant ranging from 20 to 35% by wt. of the composition, and selected from the group consisting of vitamin E, glutathione, pantethine, fucoxanthin and combinations thereof,
    wherein the pharmaceutical composition provides a synergistic effect as compared to the OEA alone, the naturally occurring BAIBA alone, or the natural anti-oxidant alone.

2. The pharmaceutical composition as claimed in claim 1, comprising Oleoylethanolamide (OEA), valine and pantethine.

3. The pharmaceutical composition as claimed in claim 1, wherein the composition further comprises natural alpha-glucosidase inhibitor, naturally occurring fatty acid amine hydrolase (FAAH) inhibitor or combination thereof.

4. The pharmaceutical composition as claimed in claim 3, wherein the natural alpha-glucosidase inhibitor is 1-deoxynojirimycin.

5. The pharmaceutical composition as claimed in claim 3, comprising from 0.5% to 1.5% by wt., of the composition, of the natural alpha-glucosidase inhibitor.

6. The pharmaceutical composition as claimed in claim 3, wherein the natural FAAH Inhibitor is Quercetin, Myricetin, Isorhamnetin, Kaempferol, Pristimerin, Curcumin, Biochanin A, Genistein, Daidzein or combination thereof.

7. The pharmaceutical composition as claimed in claim 3, comprising from 0.5% to 25% by wt., of the composition, of the natural FAAH inhibitor.

8. The pharmaceutical composition as claimed in claim 1, further comprising a pharmaceutically acceptable excipient.

9. The pharmaceutical composition as claimed in claim 8, wherein the pharmaceutically acceptable excipient is diluent, binder, lubricant, glidant or solvent.

10. The pharmaceutical composition as claimed in claim 9,
    comprising from 1% to 30% by wt., of the composition, of the diluent,
    from 0.5% to 1.5% by wt., of the composition, of the binder,
    from 0.5% to 5% by wt., of the composition, of the lubricant,
    from 1.0% to 25% by wt., of the composition, of the glidant, or
    the solvent is quantity sufficient.

11. The pharmaceutical composition as claimed in claim 1, wherein the composition is in the form of a tablet, capsule, sachet, pill, hard capsule filled with liquid or solid, soft capsule, powder, granule, suspension, solution or modified release formulation.

12. A process for preparing a pharmaceutical composition comprising a combination of: Oleoylethanolamide (OEA) ranging from 10 to 70% by wt. of the composition; naturally occurring β-aminoisobutyric acid (BAIBA) ranging from 2 to 60% by wt. of the composition, and selected from the group consisting of valine, iso-leucine and combinations thereof, and natural anti-oxidant ranging from 20 to 35% by wt. of the composition, and selected from the group consisting of vitamin E, glutathione, pantethine, fucoxanthin and combinations thereof, wherein the pharmaceutical composition provides a synergistic effect as compared to the OEA alone, the naturally occurring BAIBA alone, or the natural anti-oxidant alone, the process comprising the steps of:
    a. independently, sifting the OEA, the naturally occurring BAIBA, the natural anti-oxidant, a diluent, and a glidant,
    b. mixing the product of step a,
    c. adding a binder solution to step b to provide a dough, and sieving the dough to obtain granules,
    d. drying the granules until the level of dryness (LOD) is reduced to less than 1.5% w/w to provide semi-dried granules,
    e. sifting the semi-dried granules through a suitable sieve, and
    f. sifting a lubricant or glidant separately through a suitable sieve and adding the lubricant or glidant to the product of step e.

* * * * *